US006471686B1

(12) United States Patent
Berrigan

(10) Patent No.: US 6,471,686 B1
(45) Date of Patent: Oct. 29, 2002

(54) DRUG DELIVERY DEVICE

(76) Inventor: Thomas John Berrigan, 38 Dumfries Rd., Floreat, West Australia (AU)

( * ) Notice: Subject to any disclaimer, the term of this patent is extended or adjusted under 35 U.S.C. 154(b) by 0 days.

(21) Appl. No.: 09/186,729

(22) Filed: Nov. 4, 1998

Related U.S. Application Data

(63) Continuation-in-part of application No. 08/591,450, filed as application No. PCT/AU94/00469 on Aug. 11, 1994, now Pat. No. 5,871,478.

(30) Foreign Application Priority Data

Aug. 11, 1993 (AU) .............................................. PM 0483

(51) Int. Cl.$^7$ ................................................. A61K 9/22
(52) U.S. Cl. ..................... 604/891.1; 604/133; 604/158
(58) Field of Search .......................... 604/9, 10, 93.01, 604/131, 132, 175, 185, 891.1, 151, 153, 890.1

(56) References Cited

U.S. PATENT DOCUMENTS

| 4,525,165 A |   | 6/1985  | Fischell                |
|-------------|---|---------|-------------------------|
| 4,588,394 A |   | 5/1986  | Schulte et al.          |
| 4,681,560 A |   | 7/1987  | Schulte et al.          |
| 4,714,462 A |   | 12/1987 | DiDomenico              |
| 4,813,951 A |   | 3/1989  | Cannon                  |
| 5,053,031 A |   | 10/1991 | Borsanyi                |
| 5,085,644 A |   | 2/1992  | Watson et al.           |
| 5,137,529 A |   | 8/1992  | Watson et al.           |
| 5,607,418 A |   | 3/1997  | Arzbaecher ...... 604/891.1 |
| 5,871,478 A | * | 2/1999  | Berrigan ......... 604/891.1 |

FOREIGN PATENT DOCUMENTS

| EP | 202 696      | 11/1986 |
| EP | 488 701      | 11/1987 |
| EP | 335 671      | 10/1989 |
| EP | 0 335 671    | 10/1989 |
| EP | 342 946      | 11/1989 |
| EP | 0 342 946    | 11/1989 |
| EP | 420 620      | 4/1991  |
| WO | WO 87/06473  | 11/1987 |
| WO | WO 95/04571  | 2/1995  |

* cited by examiner

Primary Examiner—Glenn K. Dawson
Assistant Examiner—Jennifer J. Maynard
(74) Attorney, Agent, or Firm—Ladas & Parry

(57) ABSTRACT

A drug delivery device comprising a holding reservoir, a pump, a delivery reservoir and an outlet, said holding reservoir being connected to said delivery reservoir through said pump by a connection, said pump being operable manually whereby fluid is transferred from the holding reservoir to the delivery reservoir, said delivery reservoir being connected to the outlet through a flow restriction which controls flow to the outlet, said delivery reservoir being resiliently expandable from a minimum volume to a maximum volume whereby the pressure induced on the fluid within the delivery reservoir between a first volume and a second volume provides a generally constant rate of fluid delivery where the first volume is greater than the second volume and wherein the connection between the holding reservoir and the delivery reservoir permits flow only from the holding reservoir to the delivery reservoir while the pressure within the delivery reservoir is less than a maximum pressure, said connection having a control means for redirecting flow to the holding reservoir upon the pressure within the delivery reservoir attaining said maximum pressure.

40 Claims, 8 Drawing Sheets

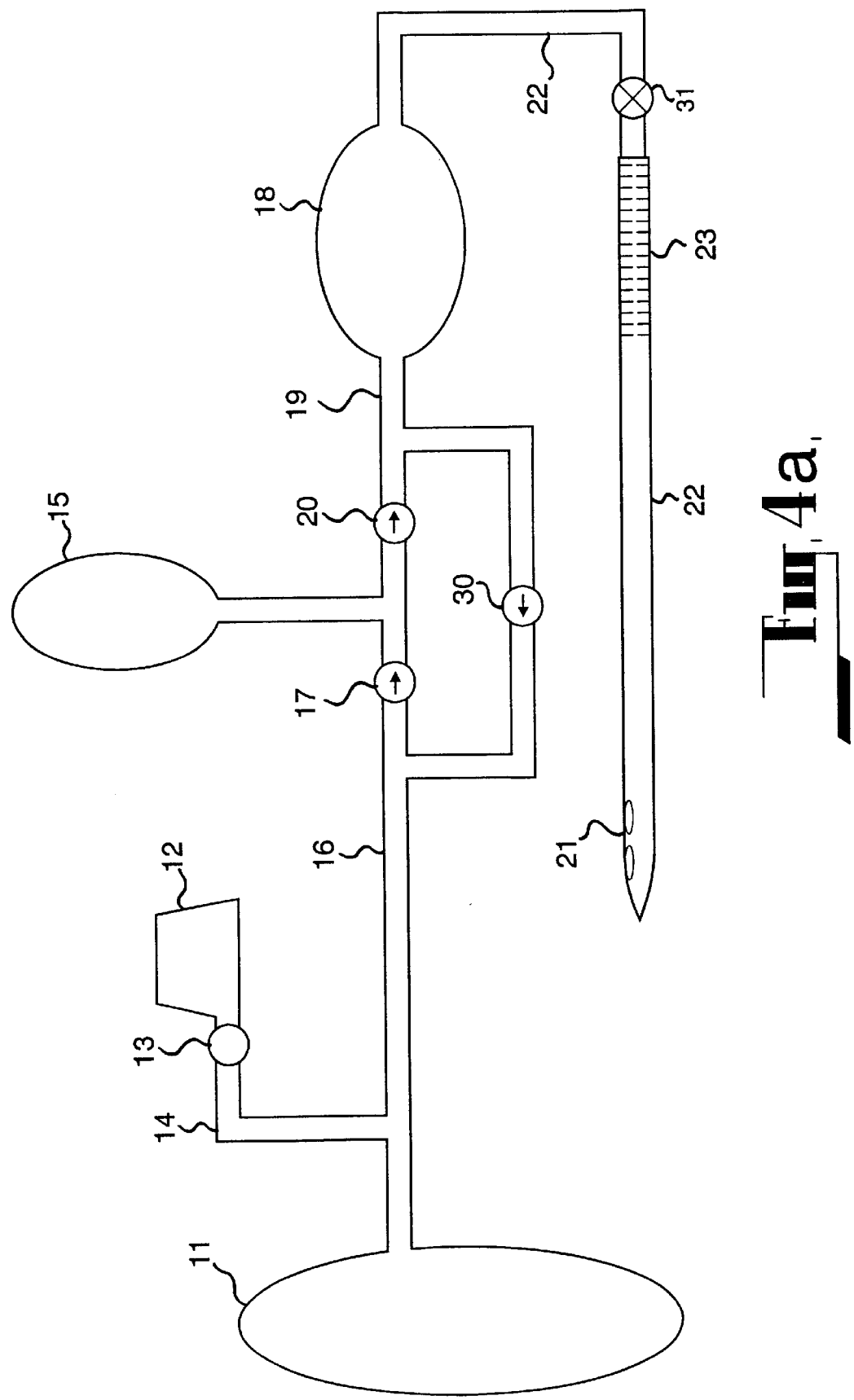

DRUG DELIVERY DEVICE

This invention relates to a drug delivery device and the application is a continuation-in part application of application Ser. No. 08/591,450, filed on Jan. 31, 1996, which is now U.S. Pat. No. 5,871,478; which is a U.S. national stage completion of International Application No. PCT/☐ AU 94/00469, filed on Aug. 11, 1994, incorporated by reference herein.

BACKGROUND OF THE INVENTION

In the treatment of patients it is often desirable to provide a means whereby a drug or like agent can be introduced in a controlled manner over an extensive period of time. With the conventional intake of drugs and the like by means of periodic ingestion of a capsule or tablet, or periodic injection, there is usually an initial significant increase in the amount of the active agent in the body which is then reduced over a period of time, until the next tablet is taken or injection given.

In many cases it is preferable to provide an intake of drug in a controlled manner such that the amount of drug in the body remains substantially constant. This is particularly the case in the treatment of patients suffering constant pain as in the case of terminally ill patients who require a constant amount of an analgesic to be administered in order for them to be able to withstand the pain.

In the past several devices have been proposed for controlling the introduction of the drug into a body whereby it can be delivered in a controlled manner over a period of time. Such devices have comprised pumps driven by a power source, which controls the delivery of drug to the body. Some of these pumps may be mounted externally to the body and are connected to a catheter introduced to a the body of the patient. Other devices have comprised a pump which is mounted subcutaneously to the body of the patient and which delivers a drug to the body at a desired location. Such devices suffer the disadvantage however they are quite expensive and that they utilise a power source in order to effect the delivery of the drug. In the event of the failure of the power source, the pump must be replaced. The power source has in the past taken a variety of forms including utilisation of a phase-change fluid as is the case of a device marketed under the trade mark "INFUSAID".

Other delivery devices have comprised a manually operated pump which may be mounted externally to the body or subcutaneously in the body of the patient whereby the pump can be activated by the patient for the delivery of the drug as need arises for that drug. Examples of such devices are disclosed in U.S. Pat. Nos. 4,588,394, 4,681,560 and 5,085,644 the contents of which are included herein by reference, and comprise devices whereby a pumping chamber is connected via catheter directly into the body and derives its source of drug from a holding reservoir. The pumping chambers are of the form whereby they are biased to a maximum volume condition, and on activation by the patient it is moved to a minimum volume position. In the case of 5,085,644 the re-entry of the drug into the pumping chamber is controlled by means of a capillary such that the pump is only able to deliver a full volume after a predetermined period of time. However, the disadvantage with this form of delivery means is that drug levels within the body will vary periodically whereby on activation of the pump, the drug level within the body initially has a high level which is then allowed to decay over a period of time until the pump is reactivated.

SUMMARY OF THE INVENTION

It is an object of this invention to provide a drug delivery means whereby the delivery of the drug to the patient can be controlled in order that there is a generally constant delivery of the drug for a period of time without the need for any form of power source. According to the invention there will be some variation in the flow rate but in comparison to the magnitude of the flow rate the variation is not significant in regard to the desired administered rate of the drug. It is an object of the invention to maintain the delivery rate within the range of desired administration rates for the drug being administered.

Accordingly the invention resides in a drug delivery means comprising a holding reservoir, a pump, a delivery reservoir and an outlet, said holding reservoir being connected to said delivery reservoir through said pump, said pump being operable manually whereby fluid is transferred from the holding reservoir to the delivery reservoir, said delivery reservoir being connected to the outlet through a flow restriction means which controls flow to the outlet, said delivery reservoir being formed to be resiliently expandable from a minimum volume to a maximum volume whereby the pressure induced on the fluid within the delivery reservoir between a first volume and a second volume is generally constant where the first volume is greater then the second volume and wherein the connection between the holding reservoir and the delivery reservoir permits flow only from the holding reservoir to the delivery reservoir while the pressure within the delivery reservoir is less than a predetermined pressure, said connection having a control means for preventing further delivery of fluid from the pumping means to the delivery reservoir on the pressure within the delivery reservoir attaining a predetermined pressure.

According to a preferred feature of the invention the first volume is equal to the maximum volume.

According to a preferred feature the first volume is less than the maximum volume.

According to a further preferred feature the second volume is equal to the minimum volume.

According to a further preferred feature the second embodiment is greater than the minimum volume.

In one form the control means comprises a first valve between the holding reservoir and the pump, and a second valve between the pump and the delivery reservoir, said first and second valves permitting unidirectional flow to the pump and delivery reservoir respectively when said delivery reservoir is not filled to its maximum volume and the pressure within the delivery reservoir is less than the predetermined pressure, the second valve permitting flow to the holding reservoir while the pressure within the delivery reservoir is at least equal to the predetermined pressure.

According to an alternative form the control means incorporates a unidirectional flow first valve between the holding reservoir and pump and a relief chamber between the pump and the delivery reservoir, said relief chamber being resiliently expandable with the expandable portion of the wall of the chamber having a higher modulus of elasticity than the delivery reservoir whereby the expandable portion will expand on the pressure between the pump and delivery reservoir being at least equal to the predetermined pressure.

In another form the control means may comprise a relief valve located between the delivery reservoir and the holding reservoir which will permit flow from the delivery reservoir to the holding reservoir when the fluid pressure in the delivery reservoir is at least equal to the predetermined pressure.

According to a preferred feature the flow restriction means comprises a single passageway and a filter located upstream from the passageway.

According to a preferred feature of the invention the flow restriction means is formed with a plurality of flow pathways. In one form the flow restriction means may comprise a plurality of capillary passageways. In one form the flow restriction means comprises a porous element. The porous element can be formed of glass, ceramic or a like inert material.

According to a further preferred feature a control valve is mounted between the delivery reservoir and the outlet, said control valve being adapted to open to allow fluid flow to the outlet on the pressure on the delivery reservoir exceeding a preset pressure wherein the preset pressure is less than the maximum. According to one embodiment the preset pressure is substantially equal to the pressure induced on the fluid in the delivery reservoir when the delivery reservoir is at its second volume. According to another preferred feature a bypass line is provided between the inlet and outlet of the control valve and a second flow restriction as provided in the bypass line.

The invention would be more fully understood in the light of the following description of several specific embodiment. The description is made with reference to the accompanying drawings of which:

BRIEF DESCRIPTION OF THE DRAWINGS

FIGS. 4a and 4b are schematic illustrated form of the fifth embodiment;

DESCRIPTION OF THE PREFERRED EMBODIMENT

Each of the embodiments are intended as subcutaneous implantable drug delivery means which are formed of a suitable material to enable the implantation within a body cavity without the danger of formation of adhesions or like conditions.

Figure 1:
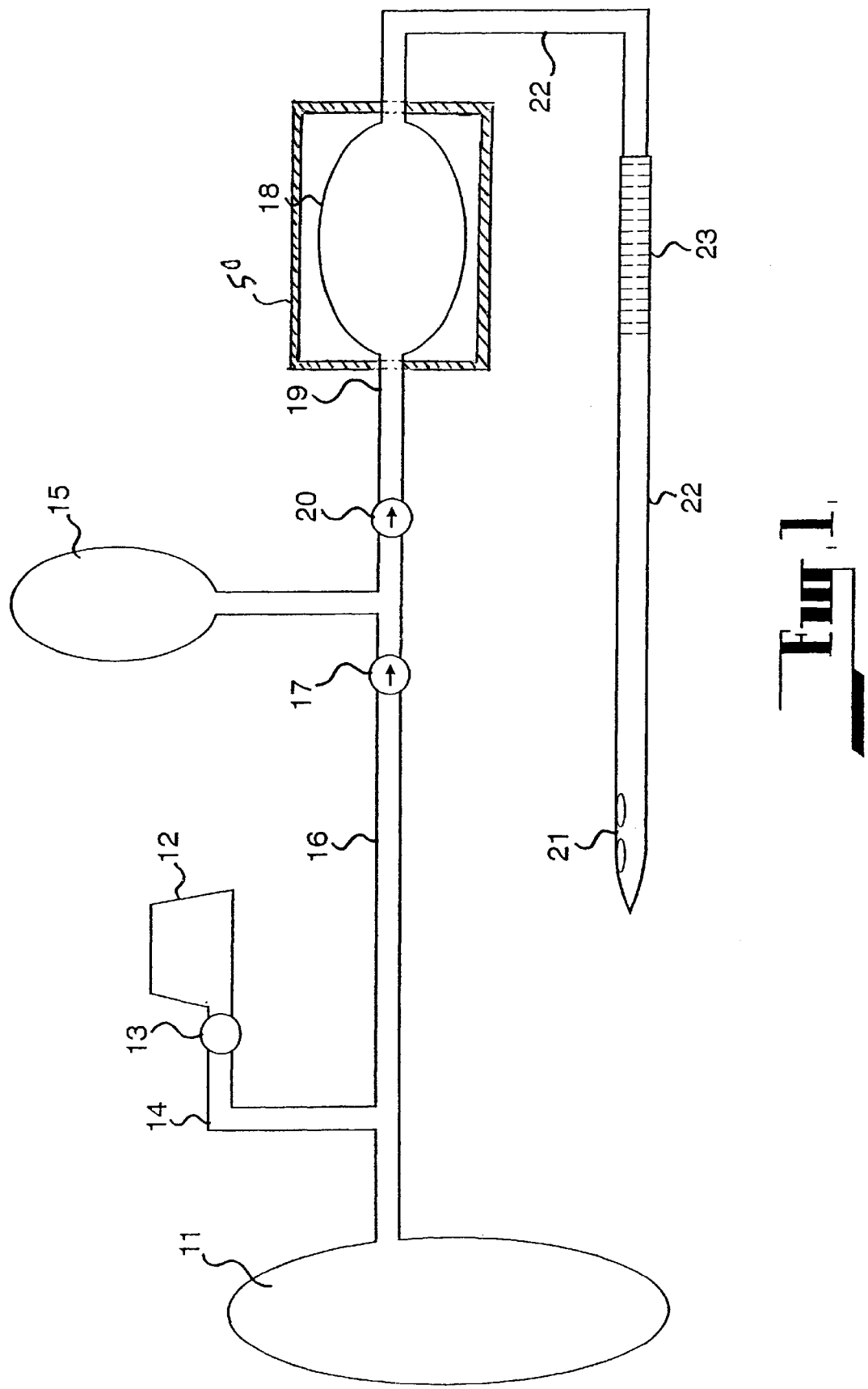
FIG. 1 is a schematic illustration of the first embodiment.

The first embodiment as shown at FIG. 1 comprises a holding reservoir 11 which is associated with a injection port 12 which is also mounted within the body and which is adapted to receive the needle of an injection syringe whereby the holding reservoir 11 can be filled. The injection port 12 is connected through a filter 13 by means of an inlet duct 14. An example of a suitable port is disclosed in U.S. Pat. No. 5,137,529 the contents of which are incorporated herein by reference.

The delivery means further comprises a pump 15 which is connected to the holding reservoir 11 through a first delivery line 16. The flow of fluid through the first delivery line 16 to the pump 15, is controlled by means of a first valve 17. The pump comprises a patient activated pump which is located in a body cavity of the patient such that it is accessible to be manipulated by the patient. The pump comprises a chamber which is biased to a maximum volume condition whereby on depression of the chamber as a result of manipulation by the patient, the chamber is caused to decrease in volume to deliver the contents of the chamber. The pump 15 is connected to a delivery reservoir 18 through a second delivery line 19. The flow of fluid from the pump 15 to the delivery reservoir 18 is controlled by means of a second valve 20. The delivery reservoir 18 is formed to be resiliently expandable or self inflating. To achieve this, at least a portion of the wall of the delivery reservoir 18 is resiliently expandable such that the delivery reservoir can be inflated.

The first valve 17 is essentially a unidirectional valve whereby there can be unidirectional flow, from the holding reservoir 11 to the chamber of the pump 15. The second valve 20 is primarily a unidirectional valve whereby there is a unidirectional flow of fluid from the chamber of the pump 15 to the delivery reservoir 18.

On the activation of the pump 15 by the patient causing the chamber of the pump 15 to collapse, fluid is delivered from the pump 15 into the delivery reservoir 18 and with repetitive activation of the pump 15 the delivery reservoir 18 is resiliently inflated to be filled by the drug.

The delivery reservoir 18 is capable of resiliently expanding from its minimum volume to its maximum volume and whereby during such period of expansion a pressure is induced on the contents of the delivery reservoir by the resilient portion of the wall of the delivery chamber. The resilience of the wall of the delivery reservoir is such that the pressure which is applied to the fluid between a first volume which is equal to the maximum volume and a second volume which is greater than the minimum volume is substantially constant throughout the expansion range of the delivery reservoir between the second and first volume.

The delivery reservoir is provided with a limiting means which serves to limit the volume the delivery reservoir to its maximum volume. The limiting means for controlling the maximum volume of the delivery reservoir may comprise a rigid container which surrounds the delivery reservoir 18 and which limits the expansion of the delivery reservoir beyond a maximum volume. Another alternative embodiment may comprise utilisation of reinforcing ribs or fibres accommodated within the expandable portion of the wall of the delivery reservoir which enables resilient expansion of that portion of the wall to a position corresponding to the maximum volume position of the delivery reservoir in order that there is substantially little expansion beyond that point. In another embodiment the means for controlling the maximum volume of the delivering reservoir may comprise a flexible enclosure having non expandable walls. The enclosure may be formed of a suitable cloth or mesh.

The first and second valves 17 and 20, while being unidirectional to allow for the delivery of fluid from the holding reservoir to the pump 15 and then to the delivery reservoir 18 are able to be rendered substantially bidirectional or unidirectional in the opposite direction at pressures above a predetermined pressure. Such valves are designed to allow flow in one direction at a specified primary pressure and then in the other direction at a secondary pressure. The effect of such is that on the delivery reservoir 18 attaining its maximum volume a back pressure is induced in the second delivery line 19, and then subsequently within the chamber of the pump 15 and the portion of the first delivery line 16 between the first valve 17 and the pump 15. On further activation of the pump, the relief property of the second valve 20 ensures that the pressure that can be induced within the delivery reservoir cannot exceed a predetermined level and this serves to prevent inflation of the delivery reservoir 18 beyond its maximum volume. This relief property of the first valve 17 also serves to ensure that on activation of the pump 15 when the delivery reservoir 18 is at it's maximum volume the contents of the chamber of the pump chamber 15 will be returned to the holding reservoir 11.

The delivery reservoir 18 is connected to an outlet 21 which may take any desired form according to the application of the delivery means through an outlet line 22. The outlet line 22 is provided with a flow restriction means 23 which comprises a means of ensuring a controlled flow from the delivery reservoir 18 to the outlet 21. The flow restriction means is formed with a plurality of passageways and may comprise an element having a plurality of capillary passageways or may comprise a porous element formed of glass, ceramic or a like inert material which is able to withstand the pressure created in the outlet line 22 by the delivery reservoir 18 such that a controlled quantity of fluid is allowed to pass through the flow restriction means.

The difference in volume of the delivery reservoir 18 between its second volume and its maximum volume is such that it is able to deliver the drug to the outlet 21 by means of the flow restriction means 23 over an extensive period of time which will be significantly greater than the intended periods between the activation of the pump.

In use the embodiment is mounted subcutaneously within the body of the patient with the injection port 12 being located at an appropriate injection site on the body and with the pump 15 located in a position at which it is accessible to the patient (eg. above the sternum). The outlet 21 is located in the appropriate portion of the body according to the application of the embodiment. The dimensions of the device are such that the embodiment can be introduced into the body through a single small incision.

Once in position, the holding chamber 11 is filled with the drug through the injection port 12. To activate the embodiment, the pump 15 is then operated by the patient, by repetitive depression of the chamber of the pump 15 such that fluid is caused to flow from the holding reservoir, through the first delivery means 16, past the first valve 17, into the chamber of the pump 15, past the second valve 20 and through the second delivery lines 19 to the delivery reservoir 18. On the delivery reservoir 18 achieving its maximum volume any further activation of the pump 15 by the patient will not cause any further delivery into the delivery reservoir 18. Once the delivery reservoir 18 has sufficient fluid introduced into it cause it to expand beyond its minimum volume, a pressure will be exerted upon that fluid which will cause delivery to the outlet 21 through the flow restriction means 23. In use the patient would be instructed to activate the pump 15 at periods well short to the period of time required for the delivery reservoir 18 to contract from its maximum volume to its second volume such that the delivery reservoir 18 will maintain a volume greater than the second volume and preferably substantially close to its maximum volume.

As a result of the embodiment, the drug is introduced into the patient from the outlet 21 at a substantially constant rate. Furthermore because the flow restriction means 23 is provided with a plurality of passageways, the blockage of any one or more passageways does not prevent continued flow of fluid to the outlet 21 which insures that the embodiment can continue operating in the event of any such partial blockage.

Figure 2:
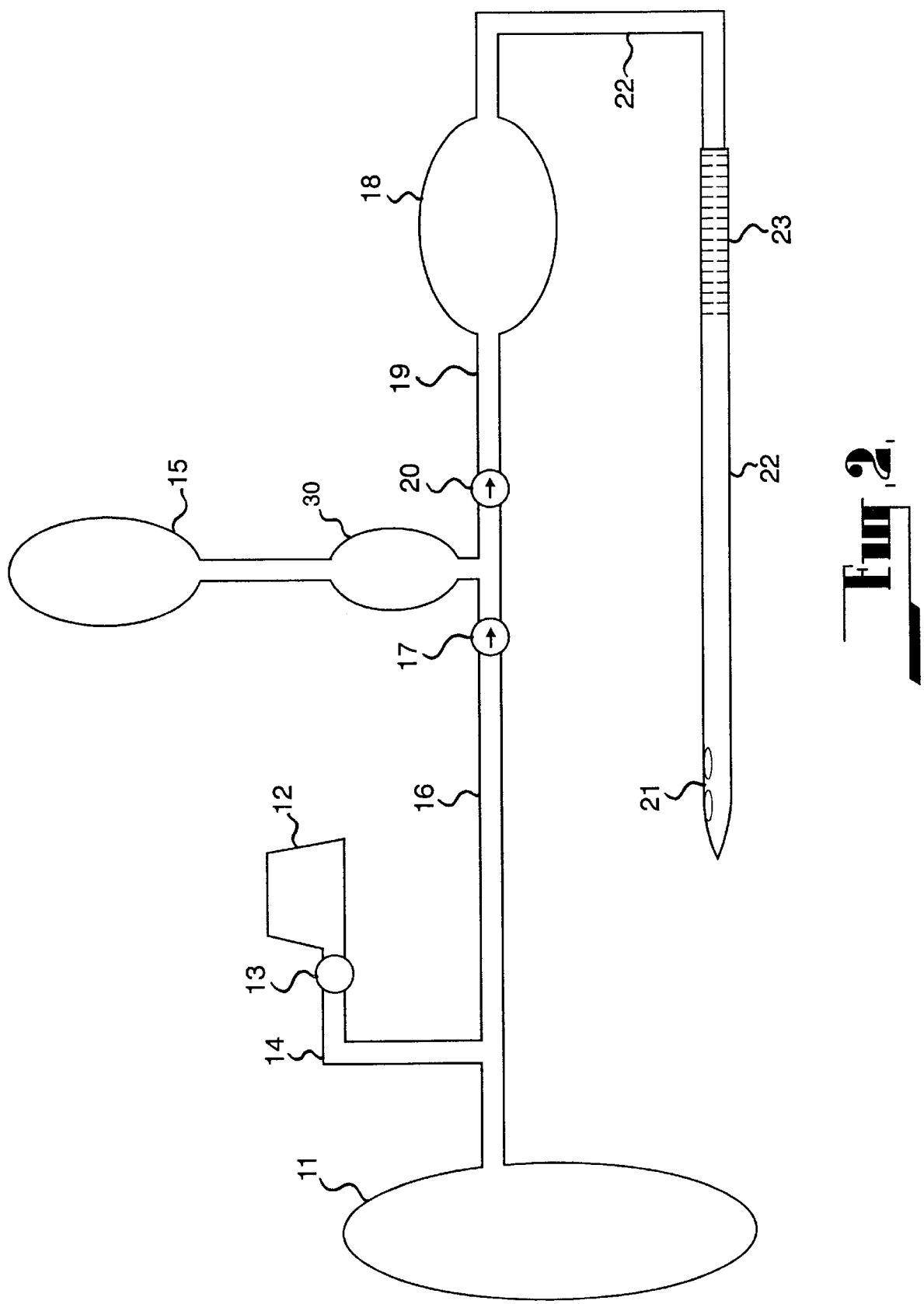
FIG. 2 is a schematic illustration of the second embodiment.

The second embodiment as shown in FIG. 2 is of almost similar form to that of FIG. 1 and the description of the first embodiment is directly applicable to the second embodiment. As a result the same reference numerals have been used in FIG. 1 for corresponding components.

The difference between the first and second embodiments comprises the presence of a relief chamber 30 between the chamber of the pump 15 and the second valve 20. In addition, the first valve 17 and second valve 20 may comprise bidirectional valves of the form utilised in the first embodiment or alternatively may comprise unidirectional valves. The relief chamber 30 is formed to be resiliently expandable and the expandable walls of the chamber have a modulus of elasticity which is greater than that of the delivery reservoir 18. The effect of such is that on activation of the pump 15 causing the delivery of fluid to the chamber from the pump the delivery reservoir 18 is inflated in preference to the relief chamber 30 until such time as the delivery chamber 18 has achieved its maximum volume. On the delivery reservoir achieving its maximum volume, the back pressure created within the second delivery line 19 is such that as the pump 15 is activated causing collapse of its chamber so the relief chamber 30 is caused to inflate. On pressure being taken from the pump 15 to cause the natural expansion of the chamber of the pump, the fluid within the relief chamber is caused to return to the chamber of the pump 15 from the relief reservoir 30. Any continued activation of the pump 15 will merely cause inflation of the relief chamber 30 rather than any expansion of the delivery reservoir 18.

Figure 3:
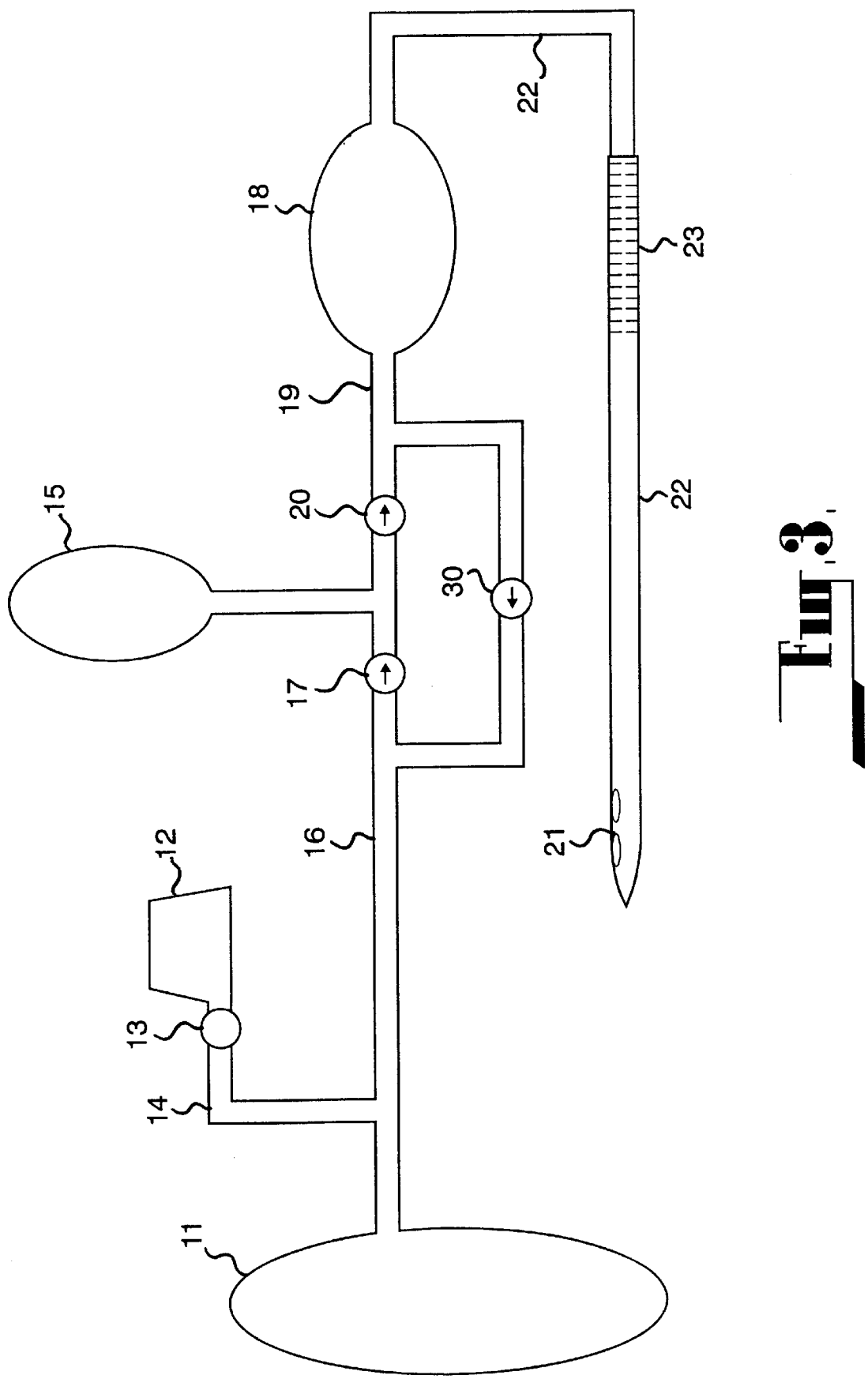
FIG. 3 is a schematic illustration of the third embodiment.

A third embodiment as shown at FIG. 3 comprises a device of similar form to that of the first embodiment shown in FIG. 1 except the first and second valves 17 and 20 respectively are conventional unidirectional valves. In the case of the third embodiment, the delivery reservoir 18 is connected to the holding chamber 11 through a third valve 30 comprising a relief valve which will open on the pressure in the delivery reservoir 18 exceeding a predetermined level. The pressure at which the relief valve 30 will open corresponds to the pressure which will be achieved after the delivery chamber has attained its maximum volume.

A fourth embodiment may take the form of any of the previous embodiments except that the flow restriction means comprises a single capillary having a filter upstream from the capillary to prevent blockage of the capillary.

Figure 4B:
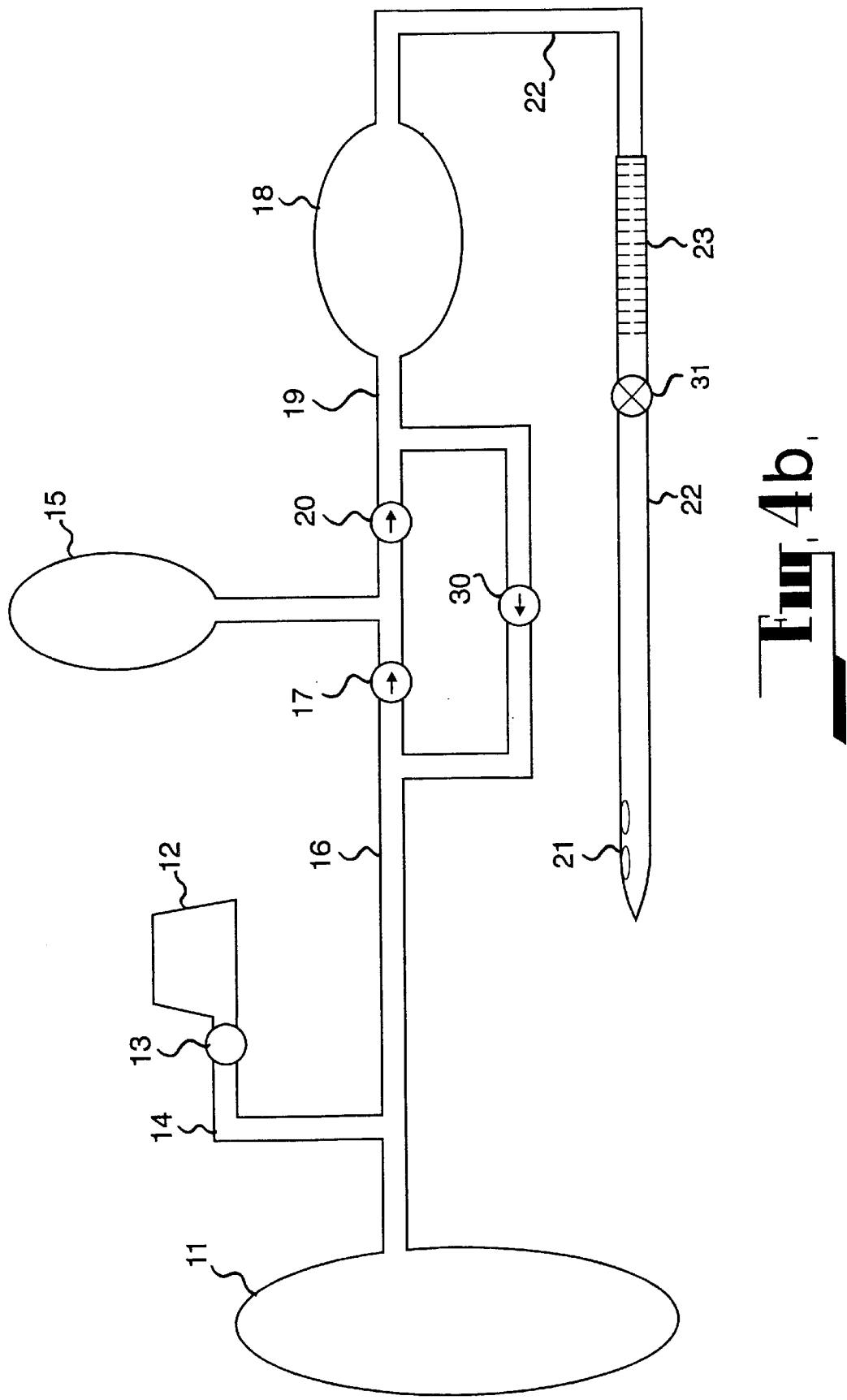

A fifth embodiment of the invention is shown schematically in two alternative forms at FIGS. 4a and 4b and comprises a variation of the previous embodiments (a variation on the 30 embodiment of FIG. 3 being shown) by location of a control valve 31 downstream from the delivery reservoir 18 and either upstream from the flow restriction means (FIG. 4a) or downstream from the flow restriction (FIG. 4b). The control valve 31 is such that it will only open above a certain preset pressure whereby when the pressure in the delivery reservoir is above the preset pressure the control valve 31 opens to enable a flow to the outlet 21. When the pressure within the delivery reservoir falls below the preset pressure the control valve 31 will close. The preset pressure of the control 31 is below the opening pressure of the pressure relief valve 30 which controls the maximum pressure in the delivery reservoir 18. The function of the control valve 31 is to allow flow from to the outlet only when the pressure in the delivery is above the preset pressure and therefore to define the second volume of the delivery reservoir 18. Therefore when the delivery reservoir is pressurised flow to the outlet 21 will only occur as long as the pressure in the delivery reservoir 18 is above the preset pressure of the control valve 31. When the pressure in the delivery reservoir falls below the preset pressure of the valve 31 the flow to the outlet will cease. This serves to prevent delivery from the outlet 21 when the pressure in the delivery reservoir has decayed to an unsatisfactory level.

Situations in which the function of the fifth embodiment may be found useful (but not limited to) the following:
1. when it is desired to keep the flow from the device reasonably constant for as long as it is considered necessary and to cause the flow to cease abruptly unless the patient maintains the pressure in the delivery reservoir above the preset pressure;
2. when it is desired to allow flow to the outlet to occur for a limited time only unless the patient keeps the pressure in the delivery reservoir above the preset pressure.

The duration of the flow through the outlet will be a function of the pressure/volume characteristics of the delivery reservoir 18 and the difference between the opening pressure of the relief valve 30 and the preset pressure of the control valve 31 and the amount of flow allowed by the flow restriction means.

Figure 5:
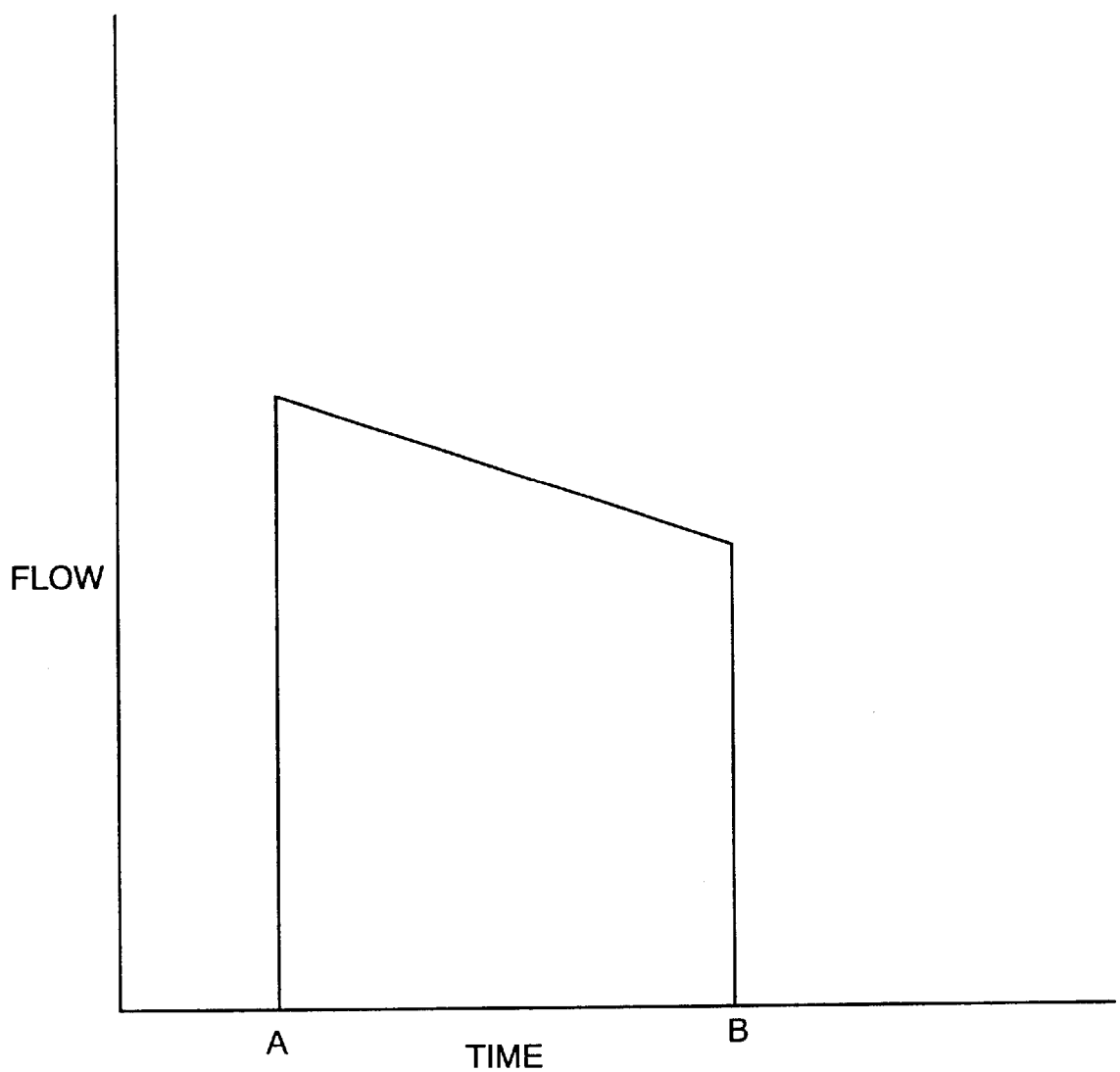
FIG. 5 is a graphical representation of the flow pattern of the fifth embodiment.

To illustrate the operation of the fifth embodiment reference is made to FIG. 5 which is a graphical illustration of the flow characteristics of the fifth embodiment. As shown at FIG. 5 when the delivery reservoir is pressurised and flow occurs at time A the fluid will be delivered from the delivery reservoir to the outlet and as a result there will be some decrease in pressure as the delivery reservoir collapsed. At a point time B when the pressure has fallen to the preset pressure of the control valve 31 the flow will cease. In this case, although there has been a reduction in the flow rate between the point in time A and the point in time B the difference is not significant in regard to the desired administration rate of the drug. Situations in which this can be used comprise administration of drugs (including analgesics) to the spinal canal.

Another example of a situation in which the embodiment may be useful would comprise the intravenous administration of analgesics for a painful condition such as migraine.

Another example in which the embodiment may be useful comprises the intravenous use of drugs to reverse cardiac arrhythmia. In this instance the patient, upon detecting the symptoms would activate the pump to pressurise the delivery reservoir and the flow of drug will occur for the period of time required to correct the condition and then cease.

Figure 6:
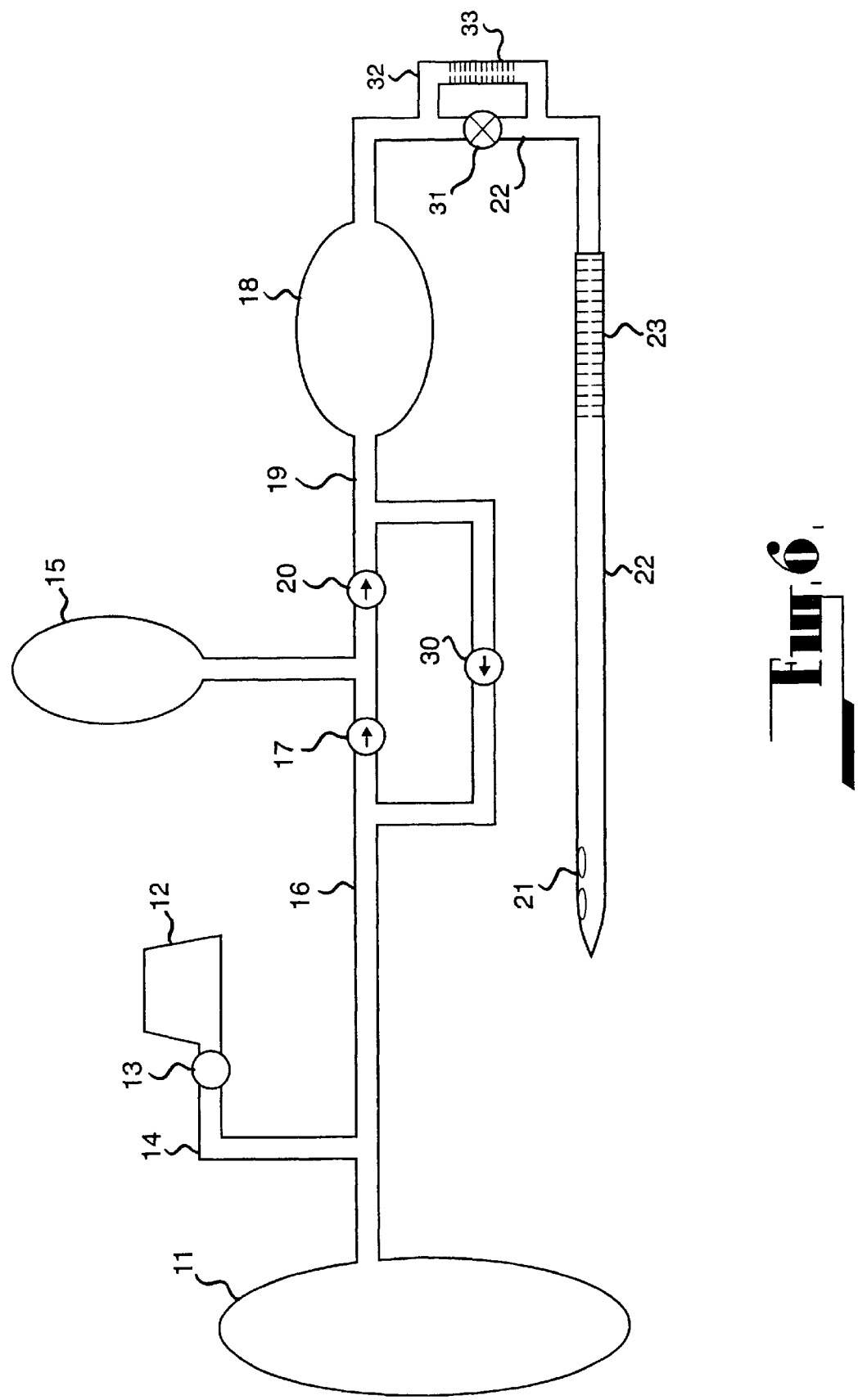
FIG. 6 is a schematic illustration of the sixth embodiment.

The sixth embodiment as shown at FIG. 6 comprises a variation of the fifth embodiment and comprises providing a bypass 32 around the control valve 31. The bypass has a second flow restriction means 33 incorporated in it. The bypass functions as a "bleed line" which will allow a restricted or background flow even when the control valve 31 is closed. The sixth embodiment can have application in situations when it is considered desirable to have a constant restricted or background flow of fluid to allow a "background" level of drug delivery and/or to keep flow occurring through the outlet to flush the line and prevent occlusion.

Figure 7:
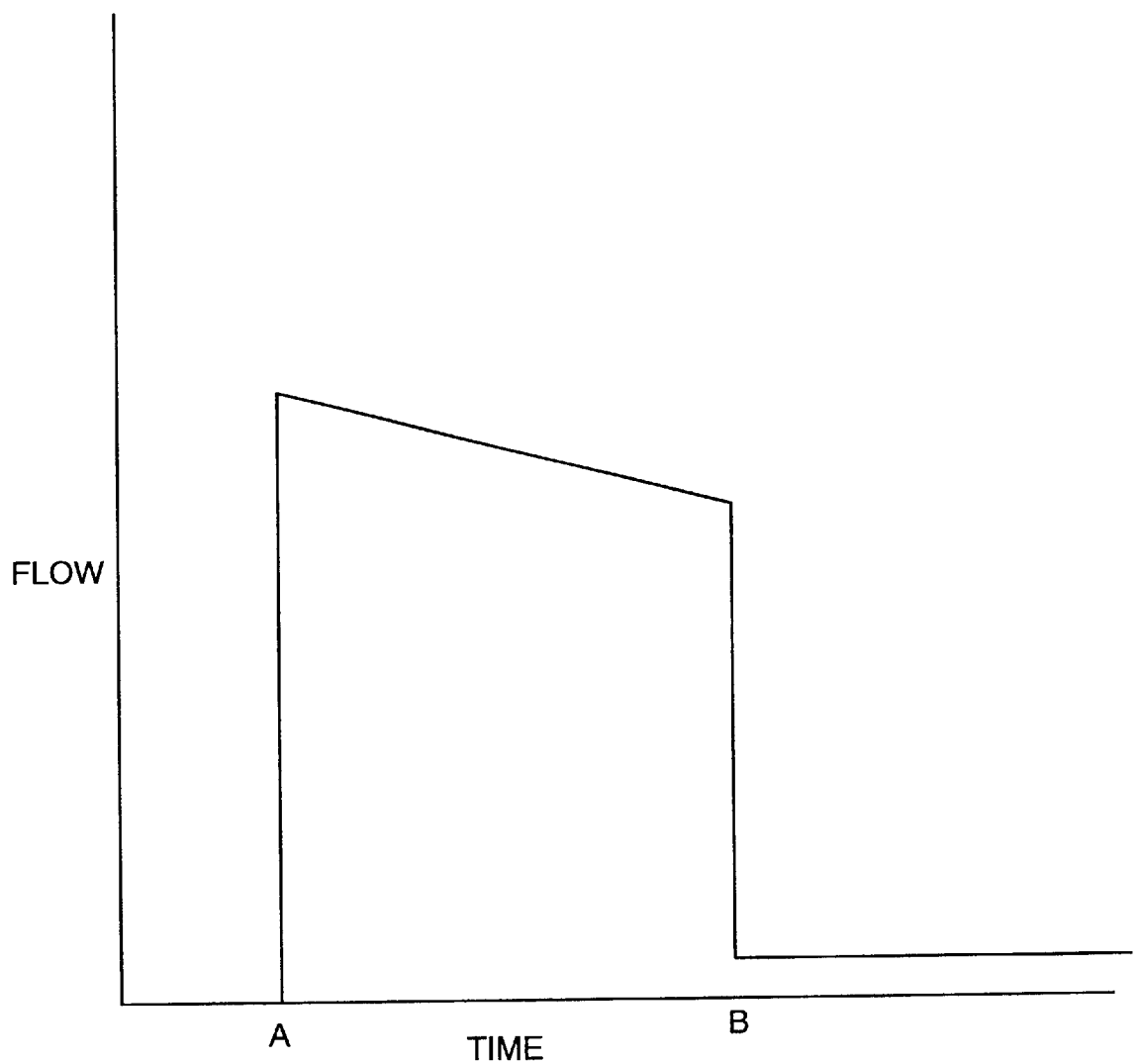
FIG. 7 is a graphical representation of the flow pattern of the sixth embodiment.

The flow characteristics of the sixth embodiment are illustrated at FIG. 7. As shown, at point in time A when the delivery reservoir has been pressurised above the preset pressure of the control valve 31 flow occurs and will continue until a point in time B is reached when the pressure within the delivery reservoir falls below the preset pressure of the control valve 31 at which time the control valve 31 is closed to prevent flow through the control valve 31. However, flow will still occur through the bypass line 32 at a reduced rate.

According to a further embodiment the control valve 31 and by-pass 33 of the sixth embodiment may be located between the first flow restrictor 23 and the outlet 21.

Throughout the specification, unless the context requires otherwise, the word "comprise" or variations such as "comprises" or "comprising", will be understood to imply the inclusion of a stated integer or group of integers but not the exclusion of any other integer or group of integers.

It should be appreciated that the scope of the present invention as claimed is not to be limited with the scope of the embodiments described above. In particular while the embodiments comprise subcutaneous implantable drug delivery means the invention need not be so limited and may comprise an externally mounted device connected to the body of a patient by a catheter or the like.

What is claimed is:

1. A drug delivery device comprising a holding reservoir, a pump, a delivery reservoir, and an outlet, said holding reservoir being connected to said delivery reservoir through said pump by a connection, said pump being operable manually whereby fluid is transferred from the holding reservoir to the delivery reservoir, said delivery reservoir being connected to the outlet through a flow restriction which controls flow to the outlet, said delivery reservoir being resiliently expandable from a minimum volume to a maximum volume, whereby a pressure that is induced on the fluid within the delivery reservoir between a first volume and a second volume provides a generally constant rate of fluid delivery, wherein the first volume is greater than the second volume, wherein the connection between the holding reservoir and the delivery reservoir permits flow only from the holding reservoir to the delivery reservoir when the pressure within the delivery reservoir is less than a predetermined pressure, wherein said connection has a control means for redirecting flow to the holding reservoir when the pressure within the delivery reservoir attains at least the predetermined pressure, and wherein a control valve is mounted between the delivery reservoir and the outlet, said control valve being adapted to open to allow fluid flow to the outlet when the pressure within the delivery reservoir exceeds a preset pressure, wherein the preset pressure is less than a maximum pressure.

2. A drug delivery device as claimed at claim 1 wherein the first volume is equal to the maximum volume.

3. A drug delivery device as claimed at claim 1 wherein the first volume is less than the maximum volume.

4. A drug delivery device as claimed at claim 1 wherein the second volume is equal to the minimum volume.

5. A drug delivery device as claimed at claim 1 wherein the second volume is greater than the minimum volume.

6. A drug delivery device as claimed in claim 1 wherein the control means comprises a first valve between the holding reservoir and the pump and a second valve between the pump and the delivery reservoir, wherein said first valve permits unidirectional flow to the pump and said second valve permits unidirectional flow to the delivery reservoir when said delivery reservoir is not filled to its maximum volume and when the pressure within the delivery reservoir is below the predetermined pressure, wherein the first valve permits flow to the holding reservoir and the second valve permits flow to the pump when the pressure within the delivery reservoir is at least equal to the predetermined pressure.

7. A drug delivery device as claimed in claim 1 wherein the control means comprises a relief valve between the delivery reservoir and the holding reservoir which will permit flow from the delivery reservoir to the holding reservoir when the pressure within the delivery reservoir is at least equal to the predetermined pressure.

8. A drug delivery device as claimed in claim 1 wherein the flow restriction is provided with a plurality of flow pathways.

9. A drug delivery device as claimed in claim 8 wherein the flow restriction comprises a plurality of capillary pathways.

10. A drug delivery device as claimed in claim 8 wherein the flow restriction comprises a porous element.

11. A drug delivery device as claimed in claim 10 wherein the porous element is formed of glass, ceramic, or like inert material.

12. A drug delivery device as claimed in claim 1 wherein the flow restriction comprises a single passageway and a filter located upstream from the passageway.

13. A drug delivery device as claimed in claim 1 wherein the delivery reservoir is enclosed by an enclosure having non-expandable walls to prevent expansion of the delivery reservoir beyond the maximum volume.

14. A drug delivery device as claimed in claim 13 wherein the walls of the enclosure are rigid.

15. A drug delivery device as claimed in claim 13 wherein the walls of the enclosure are flexible.

16. A drug delivery device as claimed in claim 1 wherein the delivery reservoir comprises walls, wherein the walls of the delivery reservoir are adapted to be incapable of expansion beyond the maximum volume.

17. A drug delivery device as claimed at claim 1 wherein a control valve is mounted between the delivery reservoir and the outlet, said control valve being adapted to open to allow fluid flow to the outlet when the pressure within the delivery reservoir exceeds a preset pressure, wherein the preset pressure is less than a maximum pressure.

18. A drug delivery device comprising a holding reservoir, a pump, a delivery reservoir, and an outlet, said holding reservoir being connected to said delivery reservoir through said pump by a connection, said pump being operable manually whereby fluid is transferred from the holding reservoir to the delivery reservoir, said delivery reservoir being connected to the outlet through a flow restriction which controls flow to the outlet, said delivery reservoir being resiliently expandable from a minimum volume to a maximum volume, whereby a pressure that is induced on the fluid within the delivery reservoir between a first volume and a second volume provides a generally constant rate of fluid delivery, wherein the first volume is greater than the second volume, wherein the connection between the holding reservoir and the delivery reservoir permits flow only from the holding reservoir to the delivery reservoir when the pressure within the delivery reservoir is less than a predetermined pressure, wherein said connection has a relief chamber for receiving and accommodating fluid when the pressure within the delivery reservoir attains at least the predetermined pressure, and wherein a control valve is mounted between the delivery reservoir and the outlet, said control valve being adapted to open to allow fluid flow to the outlet when the pressure within the delivery reservoir exceeds a preset pressure, wherein the preset pressure is less then a maximum pressure.

19. A drug delivery device as claimed in claim 18 wherein the control means comprises a first valve between the holding reservoir and the pump and a second valve between the pump and the delivery reservoir, wherein said first valve permits unidirectional flow to the pump and said second valve permits unidirectional flow to the delivery reservoir when said delivery reservoir is not filled to its maximum volume and when the pressure within the delivery reservoir is below the predetermined pressure, wherein the first valve permits flow to the holding reservoir and the second valve permits flow to the pump when the pressure within said delivery reservoir is at least equal to the predetermined pressure.

20. A drug delivery device as claimed at claim 18 wherein the control means comprises a one-way first valve between the holding reservoir and the pump, said relief chamber being located between the pump and the delivery reservoir, said relief chamber having a wall with an expandable portion that is resiliently expandable, wherein the expandable portion of the wall of the relief chamber has a higher modulus of elasticity than the delivery reservoir, whereby the expandable portion will expand when the pressure between the pump and the delivery reservoir is at least equal to a maximum pressure.

21. A drug delivery device as claimed in claim 20 wherein a second one-way valve is mounted between the relief chamber and the delivery reservoir.

22. A drug delivery device as claimed in claim 18 wherein the flow restriction is provided with a plurality of flow pathways.

23. A drug delivery device as claimed in claim 22 wherein the flow restriction comprises a plurality of capillary passageways.

24. A drug delivery device as claimed in claim 22 wherein the flow restriction comprises a porous element.

25. A drug delivery device as claimed in claim 24 wherein the porous element is formed of glass, ceramic, or like inert material.

26. A drug delivery device as claimed in claim 18 wherein the flow restriction comprises a single passageway and a filter located upstream from the passageway.

27. A drug delivery device as claimed in claim 18 wherein the delivery reservoir is enclosed by an enclosure having non-expandable walls to prevent expansion of the delivery reservoir beyond the maximum volume.

28. A drug delivery device as claimed in claim 27 wherein the walls of the enclosure are rigid.

29. A drug delivery device as claimed in claim 27 wherein the walls of the enclosure are flexible.

30. A drug delivery device as claimed in claim 18 wherein the delivery reservoir comprises walls, wherein the walls of the delivery reservoir are adapted to be incapable of expansion beyond the maximum volume.

31. A drug delivery device as claimed at claim 18 wherein the first volume is equal to the maximum volume.

32. A drug delivery device as claimed at claim 18 wherein the first volume is less than the maximum volume.

33. A drug delivery device as claimed at claim 18 wherein the second volume is equal to the minimum volume.

34. A drug delivery device as claimed at claim 18 wherein the second volume is greater than the minimum volume.

35. A drug delivery device as claimed at claim 1 wherein the preset pressure is substantially equal to the pressure induced on the fluid within the delivery reservoir when the delivery reservoir is at its second volume.

36. A drug delivery device as claimed at claim 1 wherein a bypass line is provided past the control valve and a second flow restriction is provided in the bypass line.

37. A drug delivery device as claimed at claim 35 wherein a bypass line is provided past the control valve and a second flow restriction is provided in the bypass line.

38. A drug delivery device as claimed at claim 17 wherein a control valve is mounted between the delivery reservoir and the outlet, said control valve being adapted to open to allow fluid flow to the outlet when the pressure within the delivery reservoir exceeds a preset pressure, wherein the preset pressure is less than a maximum pressure.

39. A drug delivery device as claimed at claim 17 wherein the preset pressure is substantially equal to the pressure induced on the fluid within the delivery reservoir when the delivery reservoir is at its second volume.

40. A drug delivery device as claimed at claim 39 wherein a bypass line is provided past the control valve and a second flow restriction is provided in the bypass line.

* * * * *